United States Patent
Lantzsch et al.

[11] Patent Number: 5,925,788
[45] Date of Patent: Jul. 20, 1999

[54] METHOD OF PREPARING 2-TRIFLUOROMETHOXY-BENZENESULPHONAMIDE

[75] Inventors: Reinhard Lantzsch, Wuppertal; Albrecht Marhold, Leverkusen; Ernst Kysela, Bergisch Gladbach, all of Germany

[73] Assignee: Bayer Aktiengesellschaft, Leverkusen, Germany

[21] Appl. No.: 09/068,778

[22] PCT Filed: Nov. 8, 1996

[86] PCT No.: PCT/EP96/04895

§ 371 Date: May 14, 1998

§ 102(e) Date: May 14, 1998

[87] PCT Pub. No.: WO97/19056

PCT Pub. Date: May 29, 1997

[30] Foreign Application Priority Data

Nov. 21, 1995 [DE] Germany .................. 195 43 323

[51] Int. Cl.⁶ .................................................. C07C 303/00
[52] U.S. Cl. ........................ 564/90; 564/80; 564/83; 568/33; 568/35
[58] Field of Search ............... 564/80, 83, 90; 568/33, 35

[56] References Cited

U.S. PATENT DOCUMENTS

| | | |
|---|---|---|
| 2,809,194 | 10/1957 | Novello et al. |
| 3,021,368 | 2/1962 | Blank . |
| 3,829,487 | 8/1974 | Mrozik . |
| 4,452,628 | 6/1984 | Adams . |
| 4,743,294 | 5/1988 | Diehr . |
| 4,874,894 | 10/1989 | Kannan . |
| 5,670,691 | 9/1997 | Spangler . |

OTHER PUBLICATIONS

Belinskaya et al., "Pyrolysis of Lithium . . . Benzenesulfonate," Institute of Organic Chemistry, Academy of Sciences of the Ukrainian SSR. Translated from Zhurnal Organicheskoi Khimii, vol.8, No.5, pp. 1023–1026 (1972).

*Primary Examiner*—Gary Geist
*Assistant Examiner*—Jean F. Vollano
*Attorney, Agent, or Firm*—Sprung Kramer Schaefer & Briscoe

[57] ABSTRACT

2-Trifluoromethoxy-benzenesulphonamide, of the formula (I),

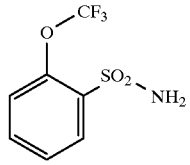

(I)

which can be used as intermediate for the preparation of certain herbicidally active compounds is obtained in very high yield and high purity by a process in which halogenated trifluoromethoxy-benzenesulphonamides of the general formula (II)

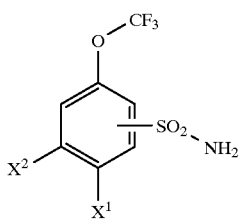

(II)

in which $X^1$ represents halogen and $X^2$ represents hydrogen or halogen are reacted with hydrogen in the presence of a catalyst and in the presence of a diluent and, if appropriate, in the presence of an acid acceptor at temperatures between 0° C. and 200° C. ("dehalogenated"), the resulting compound of the formula (I) is isolated in the customary manner in the event that "$X^2$=halogen" and converted into a pure, crystalline product by treating it with a protic polar organic liquid and isolated by removing the liquid component by means of filtration with suction in the event that "$X^2$=H".

10 Claims, No Drawings

METHOD OF PREPARING 2-TRIFLUOROMETHOXY-BENZENESULPHONAMIDE

This application is the national phase of PCT/EP96/04895 filed Nov. 8, 1996.

The invention relates to a new process for the preparation of 2-trifluoromethoxy-benzenesulphonamide, which is known as starting material for herbicidally active compounds.

It is known that 2-trifluoromethoxy-benzenesulphonamide is obtained when 2-trifluoromethoxy-benzene sulphochloride is reacted with ammonia (cf. Zh. Org. Khim. 8 (1972), 1023–1026 (russ.) a.k.a. J. Org. Chem. USSR 8 (1972), 1032–1035 (engl.)—cited in Chem. Abstracts 77:61964; cf. also U.S. Pat. No. 4,732,711).

While this reaction proceeds smoothly and yields 2-trifluoromethoxy-benzenesulphonamide in high yields and in good quality, the trifluoromethoxy-benzene sulphochloride required as starting material must be prepared beforehand from 2-trifluoromethoxy-aniline via a so-called Meerwein reaction, which, when carried out technically, is relatively complicated. Moreover, 2-trifluoromethoxy-aniline, which is required as a precursor, is available in limited quantities only.

It has now been found that 2-trifluoromethoxy-benzenesulphonamide, of the formula

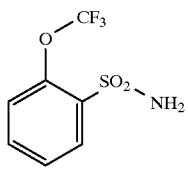
(I)

is obtained in very good yields and in high purity when halogenated trifluoromethoxy-benzenesulphonamides of the general formula (II)

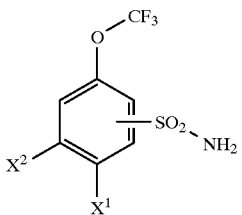
(II)

in which

X$^1$ represents halogen and

X$^2$ represents hydrogen or halogen are reacted with hydrogen in the presence of a catalyst and in the presence of a diluent and, if appropriate, in the presence of an acid acceptor at temperatures between 0° C. and 200° C. ("dehalogenated"), the resulting compound of the formula (I) is isolated in the customary manner in the event that "X$^2$=halogen" and converted into a pure, crystalline product by treating it with a protic polar organic liquid and isolated by removing the liquid component by means of filtration with suction in the event that "X$^2$=H".

The general formula (II) represents the formulae (IIA) and (IIB)

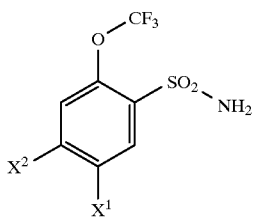
(IIA)

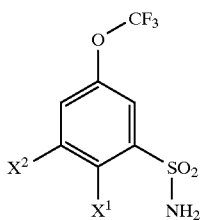
(IIB)

where in formula (IIA)

X$^1$ and X$^2$ have the abovementioned meanings and in formula (IIB)

X$^1$ has the abovementioned meaning and X$^2$ represents only hydrogen.

Surprisingly, the trifluoromethoxy group is not changed during hydrogenolytic dehalogenation. Another highly surprising feature is that, in the event that "X$^2$=H", the undesired, isomeric reaction product—3-trifluoromethoxy-benzenesulphonamide—can be dissolved by simple treatment with a protic polar organic liquid and thus removed readily, while the desired product of the formula (I) remains virtually undissolved and can thus be isolated readily by filtration with suction.

The process according to the invention is thus a valuable enrichment of the prior art.

Formula (II) provides a general definition of the halogenated trifluoromethoxy-benzenesulphonamides to be used as starting materials in the process according to the invention for the preparation of 2-trifluoromethoxy-benzenesulphonamide.

In formula (II),

X$^1$ preferably represents chlorine or bromine, and

X$^2$ preferably represents hydrogen or chlorine.

In the event that "X$^2$=H", the starting materials are employed in the form of a mixture of the compounds of the formulae (IIA) and (IIB), the compound of the formula (IIA) preferably amounting to over 60%. In the event that "X$^2$=halogen", the starting materials are those of the formula (IIA).

The starting materials of the formula (II, where X$^2$=H) are known and/or can be prepared by processes known per se (cf. EP-A 23 422, EP-A 64,322). The starting materials of the formula (II, where X$^2$=halogen) are new and also a subject-matter of the invention (cf. Preparation Examples).

The process according to the invention is carried out in the presence of a diluent. Suitable diluents are, preferably, water and organic solvents, in particular alcohols such as methanol, ethanol, n- or i-propanol, n-, i-, s- or t-butanol, ethers such as methyl t-butyl ether, methyl t-pentyl ether, ethylene gylcol dimethyl ether or tetrahydrofuran, ether alcohols such as ethylene glycol monomethyl ether or ethylene glycol monoethyl ether, furthermore hydrocarbons such as hexane, cyclohexane, methylcyclohexane, toluene or xylenes, or else mixtures of the abovementioned solvents.

Alcohols, in particular methanol and ethanol, are very especially preferably employed as diluents when carrying out the process according to the invention.

The process according to the invention is carried out in the presence of a catalyst. Suitable catalysts are, preferably, the metal catalysts conventionally used for catalytically hydrogenation reactions, if appropriate on suitable carrier materials. They preferably include (Raney) cobalt, (Raney) nickel, palladium and platinum (the latter ones optionally on a carrier material such as, for example, active charcoal, clay, kieselguhr or aluminium oxide).

Palladium on active charcoal is especially preferably employed as the catalyst in the process according to the invention.

If appropriate, the process according to the invention is carried out in the presence of an acid acceptor. Suitable acid acceptors are, generally, the inorganic or organic bases which are conventionally used. They preferably include the acetates, amides, carbonates, hydrogen carbonates, hydrides, hydroxides or alkoxides of alkali metal or alkaline earth metals, such as, for example, sodium acetate, potassium acetate, calcium acetate, lithium amide, sodium amide, potassium amide or calcium amide, sodium carbonate, potassium carbonate or calcium carbonate, sodium hydrogen carbonate, potassium hydrogen carbonate or calcium hydrogen carbonate, lithium hydride, sodium hydride, potassium hydride or calcium hydride, lithium hydroxide, sodium hydroxide, potassium hydroxide or calcium hydroxide, sodium methoxide, sodium ethoxide, sodium n- or i-propoxide, sodium n-, i-, s- or t-butoxide, potassium methoxide, potassium ethoxide, potassium n- or i-propoxide, potassium n-, i-, s- or t-butoxide; furthermore also basic organic nitrogen compounds such as, for example, trimethylamine, triethylamine, tripropylamine, tributylamine, trioctylamine, tridodecylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), and 1,8-diazabicyclo [5,4,0]-undec-7-ene (DBU).

When carrying out the process according to the invention, the reaction temperatures can be varied within a substantial range. In general, the process is carried out at temperatures between 0° C. and 200° C., preferably between 20° C. and 150° C., in particular between 40° C. and 120° C.

The process according to the invention is generally carried out under atmospheric pressure or at elevated pressure, preferably between 1 bar and 100 bar, in particular between 1 bar and 50 bar.

In a preferred embodiment of the process according to the invention, the starting compound of the formula (IIa where $X^2$=halogen) or the mixture of the starting compounds of the formulae (IIa where $X^2$=H) and (IIB) are introduced into a suitable diluent, a catalyst, and if appropriate, an acid acceptor are added, and the mixture is hydrogenated in the customary manner, preferably at elevated pressure and elevated temperature.

When the hydrogenation has ended, the remaining hydrogen is displaced with nitrogen, the mixture is diluted with water, if appropriate, and filtered. The filtrate is concentrated and the residue [which, in the event that $X^2$=H, is composed essentially of a mixture of 2-trifluoromethoxy-benzenesulphonamide and 3-trifluoromethoxy-benzenesulphonamide] is treated, that is to say stirred, with approximately twice the amount by weight of a protic polar organic liquid.

Suitable protic polar organic liquids are, in particular, optionally substituted hydroxyalkyl compounds. This group includes, preferably, alcohols such as methanol, ethanol and in each case straight-chain or branched propanols, butanols, pentanols and hexanols, furthermore alkoxyalcohols such as methoxyethanol and ethoxyethanol.

n- and i-Propanol and n-, i-, s- and t-butanol are very especially preferably used for this purpose.

The trifluoromethoxy-benzenesulphonamide, of the formula (I), which is obtained from this procedure as crystals is then isolated by filtration with suction.

The compound 2-trifluoromethoxy-benzenesulphonamide, of the formula (I), to be prepared by the process according to the invention can be used as intermediate for the preparation of herbicidally active compounds (cf. U.S. Pat. No. 4,732,711).

PREPARATION EXAMPLES

Example 1

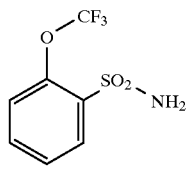

(I)

71.6 g of a mixture of 2-trifluoromethoxy-5-chloro-benzenesulphonamide (amounting to 75%) and 5-trifluoromethoxy-2-chloro-benzenesulphonamide (amounting to 25%)—total content of both compounds: 71%—is taken up in 500 ml of ethanol, treated with 5 g of palladium on charcoal (5%) and hydrogenated for 20 hours at a temperature of approx. 100° C. and an initial pressure of approx. 35 bar. After nitrogen has been passed through and the catalyst has been filtered off, the filtrate is concentrated, the residue is stirred with 260 ml of n-butanol, and the product, which has been obtained as crystals, is isolated by filtration with suction.

This gives 37.8 g (85% of theory) of 2-trifluoromethoxy-benzenesulphonamide of melting point 186° C.

Example 2

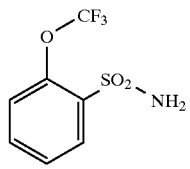

(I)

13.1 g of a mixture of 2-trifluoromethoxy-5-bromo-benzenesulphonamide (amounting to 86%) and 5-trifluoromethoxy-2-bromo-benzenesulphonamide (amounting to 14%)—total content of both compounds: 76.1%—are taken up in 40 ml of methanol and treated with a solution of 2.3 g of potassium hydroxide in 150 ml of methanol. The mixture is then treated with 1 g of palladium on charcoal (5%) and hydrogenated for 20 hours at a temperature of approx. 50° C. and an initial pressure of approx. 35 bar. After nitrogen has been passed through and the catalyst has been filtered off, the filtrate is concentrated, the residue is taken up in water, the mixture is shaken with ethyl acetate, and the organic phase is separated off, dried with sodium sulphate and filtered. The filtrate is concentrated, the residue is stirred with 40 ml of n-butanol, and the product, which has been obtained as crystals, is isolated by filtration with suction.

This gives 6.7 g (89% of theory) of 2-trifluoromethoxy-benzenesulphonamide of melting point 186° C.

Example 3

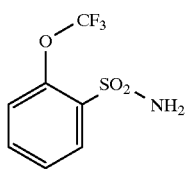
(I)

A solution of 5.6 g (0.1 mol) of potassium hydroxide in 100 ml of methanol and 0.5 g of palladium on charcoal (5%) is added to a solution of 15.5 g (0.05 mol) of 2-trifluoromethoxy4,5-dichloro-benzenesulphonamide in 60 ml of methanol. In an autoclave, the mixture is hydrogenated for 20 hours at a temperature of 75° C. under an initial pressure of 35 bar. For working-up, the catalyst is filtered off, the filtrate is treated with water and the mixture is rendered neutral. After the methanol has been distilled off, the product is filtered and dried.

This gives 9.65 g (=80% of theory) of 2-trifluoromethoxy-benzenesulphonamide of melting point 185° C.

Preparation of the Starting Compound of the Formula (IIA, Where $X^1=X^2=Cl$)

a) Step 1

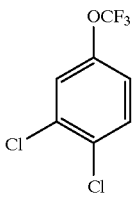

3,4-dichloro-trifluoromethoxybenzene 200 g (1.22 mol) of 3,4-dichlorophenol and 800 ml of hydrogen fluoride are introduced into a VA stainless-steel autoclave at 0° C., and 800 ml of tetrachloromethane are added. After 15 bar nitrogen have been injected, the mixture is heated to 116 to 120° C., with vigorous stirring, and the pressure of the hydrogen chloride formed is released at 28 bar. After 7 hours, the development of hydrogen chloride has ceased, whereupon the excess hydrogen fluoride together with trichlorofluoromethane formed and the excess tetrachloromethane is distilled off. Distillation of the product mixture at 60 to 86° C./17 mbar yields 213 g of distillate, of which 19.2% are 3,4-dichloro-trifluoromethoxybenzene and 80.1% are 3,4-dichloro-difluorochloromethoxybenzene.

The mixture together with 100 ml of hydrogen fluoride and 1 ml of antimony pentachloride is heated for 3 hours at 125° C., and the pressure of the hydrogen chloride formed is released at 25 bar. The distillation yields 155 g (=53% of theory) of 3,4-dichloro-trifluoromethoxybenzene of a boiling point of 62° C. at 17 mbar; content according to GC: 99.8% b) Step 2

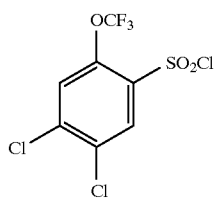

2-trifluoromethoxy-4,5-dichlorobenzene sulphochloride 50 g (0.216 mol) of 3,4-dichloro-trifluoromethoxybenzene are added dropwise at 0° C. in the course of one hour to 85 ml (1.28 mol) of chlorosulphonic acid. After 1 hour at 0° C., 17 g of thionyl chloride are added dropwise, and the mixture is subsequently heated to 40° C. Gas is evolved spasmodically.

Stirring of the reaction mixture is continued for a further 20 hours. Then, the unreacted thionyl chloride is distilled off in vacuo, and the residue, cooled to 20° C., is transferred to 150 g of ice. The product is taken up in dichloromethane and washed twice with water. The solution is distilled. In a boiling range from 96 to 102° C. at 0.4 mbar, 57 g of product distil over, content in accordance with GC: 99%, which corresponds to a yield of 80% of theory.

This compound is new and also a subject-matter of the invention.

c) Step 3

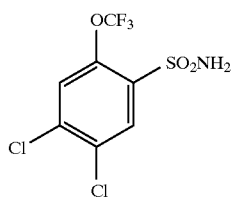

2-trifluoromethoxy4,5-dichlorobenzenesulphonamide

At 20° C., 57 g (0.173 mol) of 2-trifluoromethoxy4,5-dichloro-benzene sulphochloride are metered to 200 ml of a 25% strength ammonia solution. After stirring of the mixture has continued for 1 hour, the solid is filtered off with suction and subsequently washed with water and dried. Yield 44 g (=83% of theory); melting point 181 to 185° C.

This compound is also new and a subject-matter of the invention.

We claim:

1. Process for the preparation of 2-trifluoromethoxy-benzenesulphonamide, of the formula (I),

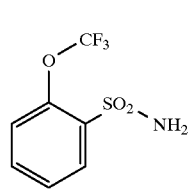
(I)

characterized in that halogenated trifluoromethoxy-benzenesulphonamides of the general formula (II)

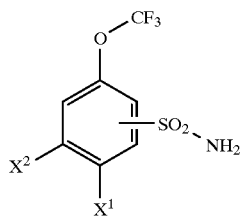

(II)

in which

X¹ represents halogen and

X² represents hydrogen or halogen are reacted with hydrogen in the presence of a catalyst and in the presence of a diluent and optionally in the presence of an acid acceptor at temperatures between 0° C. and 200° C. and the resulting compound of the formula (I) is isolated.

2. Process according to claim 1, characterized in that the reaction is carried out at temperatures between 20° C. and 150° C.

3. Process according to claim 1, characterized in that the reaction is carried out at temperatures between 40° C. and 120° C.

4. Process according to claim 1, characterized in that the reaction is carried out at a pressure between 1 bar and 100 bar, in particular between 1 bar and 50 bar.

5. Process according to claim 1, characterized in that palladium on charcoal is used as the catalyst.

6. Process according to claim 1, characterized in that an alcohol, in particular methanol or ethanol, is used as the diluent.

7. Process according to claim 1, characterized in that an optionally substituted hydroxyalkyl compound, preferably an alcohol or alkoxyalcohol, is used as the protic polar liquid.

8. Process according to claim 7, characterized in that n- or i-propanol or n-, i-, s- or t-butanol is used as the alcohol.

9. The process according to claim 1 wherein when $X^2$ represents hydrogen, said compound is converted into a pure crystalline product by treatment with a protic polar organic liquid and isolated.

10. The compounds 2-trifluoromethoxy-4,5-dichloro-benzene sulphochloride and 2-trifluoromethoxy-4,5-dichloro-benzenesulphonamide.

* * * * *